United States Patent
Hoover et al.

(10) Patent No.: US 10,540,571 B2
(45) Date of Patent: Jan. 21, 2020

(54) POLARIMETER WITH MULTIPLE INDEPENDENT TUNABLE CHANNELS AND METHOD FOR MATERIAL AND OBJECT CLASSIFICATION AND RECOGNITION

(71) Applicant: ADVANCED OPTICAL TECHNOLOGIES, INC., Albuquerque, NM (US)

(72) Inventors: Brian G. Hoover, Tijeras, NM (US); Pablo A. Reyes, Albuquerque, NM (US); David E. Taliaferro, Albuquerque, NM (US); Virgil N. Kohlhepp, III, Peralta, NM (US)

(73) Assignee: ADVANCED OPTICAL TECHNOLOGIES, INC., Albuquerque, NM (US)

( * ) Notice: Subject to any disclaimer, the term of this patent is extended or adjusted under 35 U.S.C. 154(b) by 0 days.

(21) Appl. No.: 15/542,064

(22) PCT Filed: Dec. 22, 2016

(86) PCT No.: PCT/US2016/068411
§ 371 (c)(1),
(2) Date: Jul. 6, 2017

(87) PCT Pub. No.: WO2018/118073
PCT Pub. Date: Jun. 28, 2018

(65) Prior Publication Data
US 2018/0181839 A1   Jun. 28, 2018
US 2019/0073561 A2   Mar. 7, 2019

(51) Int. Cl.
*G01N 21/21* (2006.01)
*G02B 5/30* (2006.01)
(Continued)

(52) U.S. Cl.
CPC .............. *G06K 9/6232* (2013.01); *G01J 4/04* (2013.01); *G01N 21/21* (2013.01); *G02B 5/3083* (2013.01);
(Continued)

(58) Field of Classification Search
None
See application file for complete search history.

(56) References Cited

U.S. PATENT DOCUMENTS 4,306,809 A     12/1981   Azzam
4,688,939 A  *   8/1987   Ray .................. G01N 21/95684
                                                      250/559.34
(Continued)

FOREIGN PATENT DOCUMENTS

JP     2005-181927       7/2005
JP     2012-078802       4/2012
(Continued)

OTHER PUBLICATIONS

Jahr, et al., "Hyperspectral light sheet microscopy", Nature Communications vol. 6, No. 7990, 2015, 1-7.
(Continued)

*Primary Examiner* — Kara E. Geisel
*Assistant Examiner* — Rufus L Phillips
(74) *Attorney, Agent, or Firm* — Peacock Law P.C.; Janeen Vilven

(57) ABSTRACT

Embodiments of an active or laser polarimeter are disclosed that transmit multiple independent and tunable temporally-multiplexed polarization states and record or image, at video rates if necessary, the polarized intensity or irradiance reflected or transmitted by objects illuminated by those states, and apply the recorded data to material and/or object classification and recognition using classification algorithms
(Continued)

that exploit features of polarization signatures dependent on material type, texture, and/or object shape. The polarimeter also generally records and utilizes one or more passive polarization measurements in order to realize a hybrid active-passive polarimeter. The polarimeter channels are configured and tuned to access multi-dimensional signature spaces specified by existing signature models and/or measurements, with polarization-modulator settings derived by a newly-disclosed subspace-projection algorithm that maximizes a target contrast parameter. Multiple independent polarization channels allow the new polarimeter to outperform conventional two-channel polarimeters, while the subspace-projection algorithm allows the number of channels to be minimized in order to minimize sensor size, weight, and power (SWaP) and maximize speed. Multiple channels are realized by multiplexing among independent transmitter polarization states with one or more high-speed multiplexers, in one embodiment a set of fold-mirror assemblies in the transmitter among which the laser beam is switched by one or more galvanometer scanners fitted in one embodiment with a newly-disclosed composite mirror. The method for material and object classification and recognition includes the maximally-biased classifier derived by the subspace-projection algorithm applied to a single target Mueller matrix, and methods to generalize the classifier.

53 Claims, 8 Drawing Sheets

(51) Int. Cl.
  *G02B 27/28* (2006.01)
  *G01J 4/04* (2006.01)
  *G01J 4/00* (2006.01)
  *G06K 9/62* (2006.01)
  *G06K 9/78* (2006.01)
(52) U.S. Cl.
  CPC ............. *G02B 27/283* (2013.01); *G06K 9/78* (2013.01); *G01J 2004/004* (2013.01)

(56) References Cited

U.S. PATENT DOCUMENTS

| | | | |
|---|---|---|---|
| 4,881,818 A | 11/1989 | Bustamante et al. | |
| 5,247,176 A | 9/1993 | Goldstein | |
| 5,929,443 A | 7/1999 | Alfano et al. | |
| 5,956,147 A | 9/1999 | Jellison, Jr. et al. | |
| 6,060,710 A | 5/2000 | Carrieri et al. | |
| 6,317,170 B1* | 11/2001 | Hwang | G02B 26/101 348/750 |
| 6,351,324 B1 | 2/2002 | Flint | |
| 7,218,398 B2 | 5/2007 | Smith et al. | |
| 7,333,897 B2 | 2/2008 | Stratis et al. | |
| 8,116,000 B2 | 2/2012 | Plant | |
| 2002/0027932 A1 | 3/2002 | Takada | |
| 2003/0210444 A1 | 11/2003 | Lee | |
| 2004/0012853 A1 | 1/2004 | Garcia et al. | |
| 2005/0264813 A1 | 12/2005 | Giakos | |
| 2007/0146632 A1 | 6/2007 | Chipman | |
| 2009/0116518 A1 | 5/2009 | Patel et al. | |
| 2011/0194175 A1* | 8/2011 | Dougherty | G01N 21/6458 359/386 |
| 2012/0268812 A1 | 10/2012 | Anhut et al. | |
| 2014/0009610 A1* | 1/2014 | Scherbarth | H04N 7/183 348/143 |
| 2015/0253559 A1* | 9/2015 | Kalkbrenner | G02B 21/0032 359/380 |
| 2015/0276864 A1* | 10/2015 | Yurt | G01N 21/1717 324/754.23 |
| 2016/0209270 A1 | 7/2016 | Seyfried et al. | |

FOREIGN PATENT DOCUMENTS

| | | |
|---|---|---|
| JP | 2015-527618 | 9/2015 |
| WO | 99/38046 | 7/1999 |
| WO | 2009/070160 | 6/2009 |

OTHER PUBLICATIONS

Zhang, "Viscoelasticity Measurements Inside Liposomes", Proc. of SPIE vol. 9164, 2014, 1-7.
Hoover, et al., "Polarization components analysis for invariant discrimination", Applied Optics, vol. 46, No. 34, 2007, 8364-8373.
Jones, et al., "Reflective and polarimetric characteristics of urban materials", Proc. of SPIE vol. 6240, 62400A, 2006, 1-10.
Vannier, et al., "Comparison of different active polarimetric imaging modes for target detection in outdoor environment", Applied Optics, vol. 55, No. 11, 2016, 2881-2891.

* cited by examiner

POLARIMETER WITH MULTIPLE INDEPENDENT TUNABLE CHANNELS AND METHOD FOR MATERIAL AND OBJECT CLASSIFICATION AND RECOGNITION

STATEMENT REGARDING FEDERALLY SPONSORED RESEARCH OR DEVELOPMENT

This invention was made with Government support under contract W909MY-12-C-0023 awarded by the United States Army. The United States Government has certain rights in the invention.

BACKGROUND

Embodiments of the present invention are related to the field of remote sensing or testing by polarized light examination, which comprises art from the field of polarimeters and art from the field of automated or aided discrimination, classification, and recognition of objects, materials, and material states through application of learning algorithms to polarized-light measurements. The object, material, or material state of interest is often called the target and this field of remote-sensing is often termed automated target recognition (ATR.)

Referring to FIG. 1, polarimeters can be categorized according to their radiation source as either a) active, which employ a laser or other controlled electromagnetic-radiation (EMR) source or b) passive, which employ solar or thermal electromagnetic radiation, or c) hybrid, which employ both active and passive sources. Polarimeters can be further subdivided according to the measurements they make, their polarization modulators, and their applications. Stokes polarimeters measure the Stokes parameters (or Stokes vector), which completely characterize the polarization properties of the EMR. If the source is unpolarized, as are most passive sources, then the Stokes parameters reveal all obtainable polarization properties of the illuminated object, hence Stokes polarimeters can be applied for passive remote sensing. Mueller-matrix polarimeters, as taught for instance in U.S. Pat. Nos. 4,306,809, 5,247,176, and 5,956,147, employ a controlled polarized source, often a laser, to measure the Mueller matrix, which characterizes the complete linear response of a material or object to an electromagnetic wave. U.S. Pat. No. 7,218,398 teaches application of the data obtained with a Mueller-matrix polarimeter to an inverse problem for material characterization. Ellipsometers are a subclass of Mueller-matrix polarimeters that solve the inverse problem under the assumption of no scattering or birefringence, which results in a sparse Mueller matrix, although generalized ellipsometry, as taught for instance in U.S. Pat. No. 7,218,398, relaxes certain of these assumptions. Most polarimeters designed for characterization are laboratory instruments that also comprise a sample stage to accurately control the position and orientation of the material or object sample. Polarimeters can also be categorized according to their polarization modulators. The majority of polarimeters rely on some combination of polarizing prisms or beamsplitters and rotating retarder waveplates, although alternatives including photoelastic modulators (PEM), liquid-crystal variable retarders (LCVR), and microgrid arrays have also been employed.

Polarimeters for remote sensing must be compact, light-weight, and typically fast, and their sensing schemes must work for materials and objects in generally arbitrary locations and orientations within the field-of-view. The most common approach is to limit the number of measurements or channels to 2, achievable in real-time using a polarizing prism or beamsplitter in the receiver, and to form the difference of the 2 channels. This class of polarimeter for remote sensing is taught for instance in U.S. Pat. No. 8,116,000 for passive sources and in U.S. Pat. No. 7,333,897 for active sources. Because most polarizing prisms and beamsplitters separate EMR into orthogonal polarization states (eg, vertical and horizontal linear states), most polarimeters of this type measure 2 orthogonal channels. For active 2-channel polarimeters the channels are often aligned parallel to and orthogonal to (or crossed with) the polarization direction of the illuminating EMR. Certain active polarimeters, for instance those taught in U.S. Pat. Nos. 5,956,147 and 6,060,710, employ photoelastic modulators (PEM), which require complex calibration and demodulation routines but can measure the Mueller matrix sufficiently fast for remote sensing.

In remote sensing the terms detect, discriminate, classify, recognize, and identify have formal meanings, although the terms are casually interchanged in many publications. As used herein the term "detect" means to record EMR reflected or transmitted by the target; the term "discriminate" means to distinguish the target from the background; the term "classify" means to distinguish the target or targets among various classes including the background and other non-targets, which are often referred to as clutter; the terms "recognize" and "identify" imply even more specificity. Distinguishing materials (eg, metal, plastic, or wood) is generally considered classification, while distinguishing an object as a known combination of materials and possibly shape may be considered recognition. The variability of measured data, and especially field data, requires the application of learning algorithms to anticipate the distributions of measured signatures. Learning algorithms also help exclude clutter and reduce false-alarms. Algorithms can be adapted from the field of machine-learning. Learning algorithms of varying sophistication have been applied to classify materials based on polarimeter measurements, as taught for instance in U.S. Pat. Nos. 6,060,710 and 7,333,897 and by Jones, et al., Proc. SPIE 6240, 62400A (2006) and by Hoover and Tyo, Applied Optics 46, 8364-8373 (2007).

Electromagnetic sensors that can rapidly and non-destructively discriminate, classify, and recognize materials, material states, and objects composed of those materials and states have many useful applications depending on the material sensitivities of the measured characteristics of the electromagnetic wave. Polarization at optical and near-optical frequencies is sensitive to broad ranges of materials and material states including metals, plastics, fibrous materials including fiber composites, crystals, chiral molecules, and biological tissues, and even broader ranges if patterned, stressed, or damaged materials are considered. Polarimeters have been demonstrated for the discrimination and classification of such materials and states, usually by increasing the contrast between a target material or material state and other materials or material states in the observation of reflected or transmitted EMR. Most polarimeters increase contrast by differencing irradiance channels defined by different settings of their polarization modulators. Ideally the irradiances of the target are different in the two channels, while the irradiances of non-targets are similar in the two channels, such that the difference channel provides increased target contrast. The polarimeter irradiance channels can be in the form of digital images or in the form of detector signals, multiplexed in time and/or space. For high-speed performance, polarimeters are usually limited to two simultaneous channels, as in the case of polarization-difference imaging (PDI), as taught for instance in U.S. Pat. Nos. 4,881,818, 5,929,443, and 8,116,000.

Active polarimeters comprise a source of controlled, polarized EMR, often a laser, that is typically formed into a beam that illuminates the sample or scene of interest. Compared to passive polarimeters, which utilize solar illumination or thermal emission, active polarimeters provide access to additional signature components and perform independently of weather and time-of-day. Active polarimeters designed for characterization, as taught for optical and infrared frequencies in U.S. Pat. Nos. 4,306,809, 5,247,176, 5,956,147, and 7,218,398, typically measure the complete polarization signature, also known as the Mueller matrix, for illumination at given angles and electromagnetic frequencies. These are typically large laboratory instruments with stages to control sample orientation and position and polarization modulators with high size, weight, and power (SWaP) requirements and data rates well below video rate. For instance, U.S. Pat. No. 7,218,398 specifies the maximum data rate of this type of polarimeter on the order of 1 Hz.

Mathematically, the Stokes parameters are written as $$S = [S_0 \, S_1 \, S_2 \, S_3]^T, \quad (1)$$

where $S_0$ is the irradiance, $S_1$ is the degree of linear polarization in the horizontal-vertical coordinate system, $S_2$ is the degree of linear polarization at ±45° to the horizontal-vertical coordinates, $S_3$ is the degree of circular polarization, and $[\ldots]^T$ denotes a matrix transpose. The Stokes parameters define the polarization state of the EMR. The Mueller matrix is the linear transformation of the Stokes parameters upon interaction of the electromagnetic wave with a material object, written mathematically as $$S_{out} = MS = \begin{bmatrix} M_{00} & M_{01} & M_{02} & M_{03} \\ M_{10} & M_{11} & M_{12} & M_{13} \\ M_{20} & M_{21} & M_{22} & M_{23} \\ M_{30} & M_{31} & M_{32} & M_{33} \end{bmatrix} \begin{bmatrix} S_0 \\ S_1 \\ S_2 \\ S_3 \end{bmatrix}. \quad (2)$$

For mathematical analysis and design the Mueller matrix is often written in one-dimensional form as $$\tilde{M} = [M_{00} \, M_{01} \, M_{02} \, M_{03} \, M_{10} \ldots M_{31} \, M_{32} \, M_{33}]. \quad (3)$$

The Stokes parameters are often referred to as the Stokes vector, which is correct only in the computing sense of a one-dimensional array of numbers. Since irradiance cannot be negative, both Stokes parameters and Mueller matrices lack additive inverses, so are not vectors in the algebraic sense.

Active polarimeters designed for remote sensing typically do not measure the complete Mueller matrix, but only parts of the signature that show contrast between the target of interest and the anticipated background and clutter, allowing SWaP to be reduced and speed increased due to fewer components and fewer measurements. For example, as taught in U.S. Pat. No. 7,580,127, most atmospheric aerosols and clouds exhibit a diagonal Mueller matrix with a single independent parameter that can be obtained from measurement of $M_{11}$, which can be accomplished with an active polarimeter by forming the difference of two orthogonal channels. Nearly all active polarimeters designed for remote sensing are based on measurement of one or two polarization channels, with this limitation imposed by requirements for low SWaP and/or high speed. Vannier, et al., Applied Optics 55, 2881-2891 (2016) demonstrates the current public-domain state-of-the-art in polarimeters for optical remote sensing, employing LCVR modulators and an optimization routine to empirically derive and implement a single-channel active polarimeter that provides enhanced-contrast imaging of a specific class of materials. However, as shown in Hoover and Tyo, Applied Optics 46, 8364-8373 (2007), active polarization signatures of many relevant materials are actually multi-dimensional, and discrimination, classification, and recognition performance can be improved by applying learning algorithms to measured multi-dimensional signatures. In particular, multi-dimensional measurements are usually needed to achieve classification performance that is relatively invariant to the target orientation or pose, which is usually a critical requirement for remote sensing. Fielding an active polarimeter for high-speed, high-performance classification or ATR therefore requires a new class of polarimeter that can measure specific multi-dimensional signatures while maintaining the low SWaP and high speed achievable by 2-channel polarimeters.

Most active field sensors, including polarimeters, are configured for monostatic or near-monostatic geometries, due to the practical advantage of placing the source-transmitter and the receiver-detector on the same platform. Passive sensors, on the other hand, often operate at large bistatic angles, for instance as illustrated in FIG. 2. While the dimensionality of passive polarization signatures is generally too low to achieve pose invariance or match the classification performance of active polarimeters, for certain materials and objects the passive signature contains unique information at large bistatic angles that can augment the active signature and improve performance. There is therefore a need for field polarimeters to combine active and passive signature measurements in the same hybrid polarimeter in order to utilize more information and improve remote-sensing performance.

SUMMARY OF EMBODIMENTS OF THE PRESENT INVENTION

One embodiment of the present invention provides for a registered-channel multiplexer (RCM) having a scanning element positioned to direct a beam from a controlled source of electromagnetic radiation (EMR) serially among a set of independent modulators. One version of the RCM is illustrated in FIG. 3. Each member of the set of independent modulators defines a channel that is configured to modulate a state of the beam among a set of independent states to produce a modulated beam. An assembly of reflectors is configured to redirect the modulated beam to a co-registered path that is pointed at a field-of-view. The scanning element can be a scanner mirror attached to a first mechanical scanner, for instance a galvanometer scanner, that comprises a rotation axis, and the assembly of reflectors can be an assembly of mirrors. Further still the scanner mirror can be a composite mirror comprising a flat mirror parallel to the rotation axis of the first mechanical scanner and a second wedge mirror mounted at an angle to the flat mirror, for example, at an angle of about 45 degrees. The assembly of mirrors may comprise one or more flat scanner mirrors attached to a second set of mechanical scanners. The set of independent modulators can be selected from the group consisting of lenses, polarization modulators, spectral filters, diffractive array generators, holograms, amplitude-phase masks and any combination thereof. One or more members of the set of independent modulators can be tunable, and one or more different members can be a beam block as illustrated in FIG. 4.

Another embodiment of the present invention provides for a sensor for classifying or recognizing a target or targets within a field-of-view (FOV) using multiple independent channels. The sensor comprises a source of controlled electromagnetic radiation (EMR) positioned in a path with a detector and the FOV positioned there between. The sensor includes a registered-channel multiplexer (RCM) comprising a scanning element positioned to direct a beam from the source of controlled EMR serially among a first set of independent modulators, wherein each member of the first set of independent modulators corresponds to a channel and the scanner and modulators are configured to modulate a state of the beam among a set of independent states to produce a modulated beam. An assembly of reflectors is configured to redirect the modulated beam to a co-registered path that is pointed at the FOV. An EMR collector is positioned to direct EMR reflected from or transmitted by objects within the FOV to a second modulator independent of the first set of independent modulators. The detector is positioned to receive the EMR from the second modulator, wherein the detector produces a set of signals that are synchronized with the set of channels formed by the first set of modulators and the second modulator. The first set of independent modulators and the second independent modulator can be selected from the group consisting of lenses, polarization modulators, spectral filters, diffractive array generators, holograms, amplitude-phase masks, and any combination thereof. The sensor includes a processor that is connected with a memory, wherein the processor is configured to execute a classification algorithm stored in the memory by applying a user-adjustable threshold to the set of detector signals to assign a class label (which may also be stored in memory) to the set of detector signals and wherein the classification algorithm specifies the function of the threshold in terms of the set of channels formed by the first set of modulators and the second modulator. The class label can be either binary, assuming the values 0 or 1 only, or multi-valued. The first set of independent modulators and the second independent modulator can be tunable, and one or more different members of the first set of independent modulators can be a beam block. The EMR directed by the collector to the second modulator may include EMR from a passive source illuminating or emanating from objects within the FOV, in which case the EMR directed by the collector to the second modulator while the scanning element is directed at the beam block can produce a detector signal corresponding to a passive channel as a member of the set of detector signals. In one embodiment the set of detector signals is a set of registered digital images and a class label is assigned to each pixel to form a digital classification image. The class labels can be assigned at a rate of 20 Hz or greater and for imaging the class labels can be assigned and the classification image electronically displayed at a rate of 20 frames-per-second or greater. The FOV can be scanned or swept over an area or a volume by a gimbal or a moving platform on which the sensor is mounted. Further, the set of detector signals can be synchronized with the set of channels formed by the first set of modulators and the second modulator by a lock-in amplifier using a timing signal provided by the scanning element.

Yet another embodiment of the present invention provides for a polarimeter for classifying or recognizing a target or targets within a field-of-view (FOV) using multiple independent polarization channels. The polarimeter comprises a source of controlled electromagnetic radiation (EMR) positioned in a path with a detector and the FOV positioned there between. The polarimeter includes a registered-channel multiplexer (RCM) comprising a scanning element positioned to direct a beam from the source of controlled EMR serially among a first set of independent polarization modulators. The first set of independent polarization modulators, wherein each member of the set corresponds to a polarization channel, is configured to modulate the polarization state of the beam among a set of independent polarization states to produce a modulated beam. An assembly of reflectors is configured to redirect the modulated beam to a co-registered path that is pointed at the FOV. An EMR collector is positioned to direct EMR reflected from or transmitted by objects within the FOV to a second polarization modulator independent of the first set of polarization modulators. The detector is positioned to receive the EMR from the second polarization modulator, wherein the detector produces a set of signals that are synchronized with the set of channels formed by the first set of polarization modulators and the second polarization modulator. The polarimeter includes a processor connected with a memory, wherein the processor is configured to execute a classification algorithm stored in the memory by applying a user-adjustable threshold to the set of detector signals to assign a class label (which may also be stored in memory) to the set of detector signals, wherein the classification algorithm specifies the function of the threshold in terms of the set of channels formed by the first set of polarization modulators and the second polarization modulator. The class label can be either binary, assuming the values 0 or 1 only, or multi-valued. The first set of independent polarization modulators and the second independent polarization modulator can be tunable, and one or more members of the first set of polarization modulators can be a beam block. The EMR directed by the collector to the second modulator may include EMR from a passive source illuminating or emanating from the field-of-view, in which case the EMR directed by the collector to the second modulator while the scanning element is directed at the beam block can produce a detector signal corresponding to a passive channel as a member of the set of detector signals. In one embodiment the set of detector signals is a set of registered digital images and a class label is assigned to each pixel to form a digital polarization classification image (PCI). The class labels can be assigned at a rate of 20 Hz or greater and PCIs can be electronically displayed at a rate of 20 frames-per-second or greater. The FOV can be scanned or swept over an area or a volume by a gimbal or a moving platform on which the polarimeter is mounted. Further, the set of detector signals can be synchronized with the set of channels formed by the first set of polarization modulators and the second polarization modulator by a lock-in amplifier using a timing signal provided by the scanning element. In one embodiment the channels are defined by a subspace-projection algorithm that applies a gradient operator on a vector space of reduced Mueller matrices and maximizes a resulting contrast parameter, and the user-adjustable threshold is a function of the channels derived by the subspace-projection algorithm. In another embodiment the contrast parameter and the function of the user-adjustable threshold are defined by an external machine-learning algorithm.

Yet another embodiment of the present invention provides a method for classifying or recognizing a target or targets within a field-of-view (FOV) by using a polarimeter with multiple independent channels. The method includes positioning a source of controlled electromagnetic radiation (EMR) in a path with a detector and the FOV positioned there between. The method employs a registered-channel multiplexer (RCM), which uses a scanning element to serially direct a beam from the controlled source of EMR among a first set of independent polarization modulators, producing a modulated beam, wherein each member of the set of independent polarization modulators corresponds to a channel and the set is configured to modulate the polarization state of the beam among a set of independent polarization states, and an assembly of reflectors to redirect the modulated beam to a co-registered path pointed at the FOV. The method further includes collecting a portion of the EMR reflected from or transmitted by objects within the FOV with an EMR collector that directs the EMR to a second polarization modulator independent of the first set of polarization modulators, and receiving the EMR from the second polarization modulator at the detector, wherein the detector produces a set of detector signals that are synchronized with the set of channels formed by the first set of polarization modulators and the second polarization modulator. The method applies a classification algorithm and a user-adjustable threshold to the set of detector signals to assign a class label to the set of detector signals, wherein the classification algorithm specifies the function of the threshold in terms of the set of channels formed by the first set of polarization modulators and the second polarization modulator and the class label can be either binary, assuming the values 0 or 1 only, or multi-valued. The first set of independent polarization modulators and the second independent polarization modulator can be tunable, and one or more members of the first set of polarization modulators can be a beam block. The EMR directed by the collector to the second modulator may include EMR from a passive source illuminating or emanating from objects within the FOV, in which case the EMR directed by the collector to the second modulator while the scanning element is directed at the beam block can produce a detector signal corresponding to a passive channel as a member of the set of detector signals. In one embodiment the set of detector signals is a set of registered digital images and a class label is assigned to each pixel to form a digital polarization classification image (PCI). The class labels can be assigned at a rate of 20 Hz or greater and PCIs can be electronically displayed at a rate of 20 frames-per-second or greater. The method may also include scanning or sweeping the FOV through an area or a volume using a gimbal or a moving platform on which the polarimeter is mounted. The method may also include synchronizing the set of detector signals with the set of channels formed by the first set of polarization modulators and the second polarization modulator using a lock-in amplifier that reads a timing signal from the scanning element. One embodiment includes defining the polarization channels using a subspace-projection algorithm that applies a gradient operator on a vector space of reduced Mueller matrices and maximizes a resulting contrast parameter, and the user-adjustable threshold can be a function of the channels derived by the subspace-projection algorithm. Another embodiment includes applying an external machine-learning algorithm to define the contrast parameter and the function of the user-adjustable threshold.

Another embodiment comprises a hybrid polarimeter and method of use that can achieve data rates up to video-rate in imaging mode with sufficiently small SWaP for field implementations.

The new subspace-projection algorithm specifies the set of polarization-modulator settings or channels that maximize contrast between the target or state of interest and the anticipated backgrounds and other objects or states that might be observed. Each polarimeter channel corresponds to an irradiance measurement or a detector signal, and measurements in multiple channels are generally combined to form a set of detector signals or a projection that is used to test whether the object or state corresponds to the target or not. The projection can be either a one-dimensional or multi-dimensional irradiance signal depending on the type of classification algorithm used. For a one-dimensional projection a simple irradiance threshold serves as the classifier, such that an irradiance above or below the threshold, or between two thresholds, corresponds to a positive target classification. In imaging mode every pixel is an independent sensor, and positive classifications can be represented by white pixels with all other pixels black, providing binary polarization-classification images (PCI) that are advantageous for fast interpretation and practical data transmission and storage.

The subspace-projection algorithm derives the polarimeter channels from the available polarization modulators and the Mueller matrices of the anticipated objects, materials, and/or material states, with the Mueller matrices known a priori from a model and/or training characterization measurements. The subspace-projection algorithm provides the maximally-biased one-dimensional classifier if only a single target Mueller matrix is used as input, and provides more generalized classifiers if non-target Mueller matrices are incorporated into the input (see Detailed Description.) The method can be applied to an existing polarimeter, to derive the optimal set of realizable channels, or at the polarimeter design stage to derive the minimum set of channels that can achieve the required classification or ATR performance.

Another embodiment of the present invention provides a method of enhancing the contrast of a target or targets recorded by a polarimeter. This method includes obtaining modeled or measured Mueller matrices of the target or targets and other materials or objects to be recorded by the polarimeter and applying the subspace-projection algorithm to the Mueller matrices and to the set of polarization modulators of the polarimeter to specify the settings of the polarization modulators, wherein the subspace-projection algorithm applies a gradient operator on a vector space of reduced Mueller matrices and maximizes a resulting contrast parameter. Another embodiment includes applying an external machine-learning algorithm to define the contrast parameter.

The current invention includes new hardware designs for a polarization multiplexer to achieve data rates up to video-rate in imaging mode. While passive polarimeters contain polarization modulators in the receiver only, active polarimeters comprise modulators in both the transmitter and receiver. One embodiment of the current invention employs a conventional polarization modulator, a polarizing prism, in the receiver, and a new temporally-multiplexed polarization modulator (or polarization multiplexer) in the transmitter, which is a form of the more general registered-channel multiplexer (RCM.) The RCM can assume various geometries, all of which utilize a scanner to switch or scan the beam among multiple independent and tunable states at high speed, possibly including a null state that corresponds to a passive channel. Achieving video-rate multiplexing with a mechanical scanner requires a rotor of lower inertia than the hollow-core motors used in rotating-retarder polarimeters like those taught in U.S. Pat. Nos. 4,306,809, 5,247,176, and 7,218,398. One embodiment of the invention employs a low-inertia galvanometer scanner that switches a laser beam among a set of tunable polarization modulators. Each modulator in the transmitter, in combination with a static polarizing prism in the receiver, constitutes 2 orthogonal polarimeter channels, while overall the polarimeter may have 8 or more channels. Each polarization modulator in the transmitter can be independently tuned to realize multiple arbitrary channels.

Classification of various materials on natural backgrounds has been demonstrated in field tests, at approximately 20 m horizontal range, employing the polarimeter main embodiment of the invention. Applications of the main embodiment include, but are not limited to, classification of hazardous objects for route clearance, classification of materials in mining, manufacturing, waste, and recycling streams, and real-time non-destructive testing of vehicle and structural materials including, but not limited to, fiber composites and non-cubic metals. By changing the laser frequency and/or the projection and collection optics, the invention can be customized for manufacturing applications including, but not limited to, monitoring of thin-film, textile, polymer, chiral pharmaceutical, composite material, and non-cubic metal fabrication and processing, including mechanical and laser machining. Smaller embodiments of the invention are applicable to recognition of security inks for asset tagging and product authentication, quantification of micro-plastics, biomedical-tissue assays, and general polarization microscopy, while larger embodiments that utilize high-power lasers are applicable for long-range material and object classification and recognition from resolved or unresolved imagery, for instance surveillance and reconnaissance, damage assessment, search and rescue, mapping and assessment of contaminants and debris, particularly plastics, and space-object classification.

BRIEF DESCRIPTION OF THE DRAWINGS

The accompanying drawings, which are incorporated into and form a part of the specification, illustrate one or more embodiments of the present invention and, together with the description, serve to explain the principles of the invention. The drawings are only for the purpose of illustrating one or more embodiments of the invention and are not to be construed as limiting the invention.

DETAILED DESCRIPTION

Figure 1:
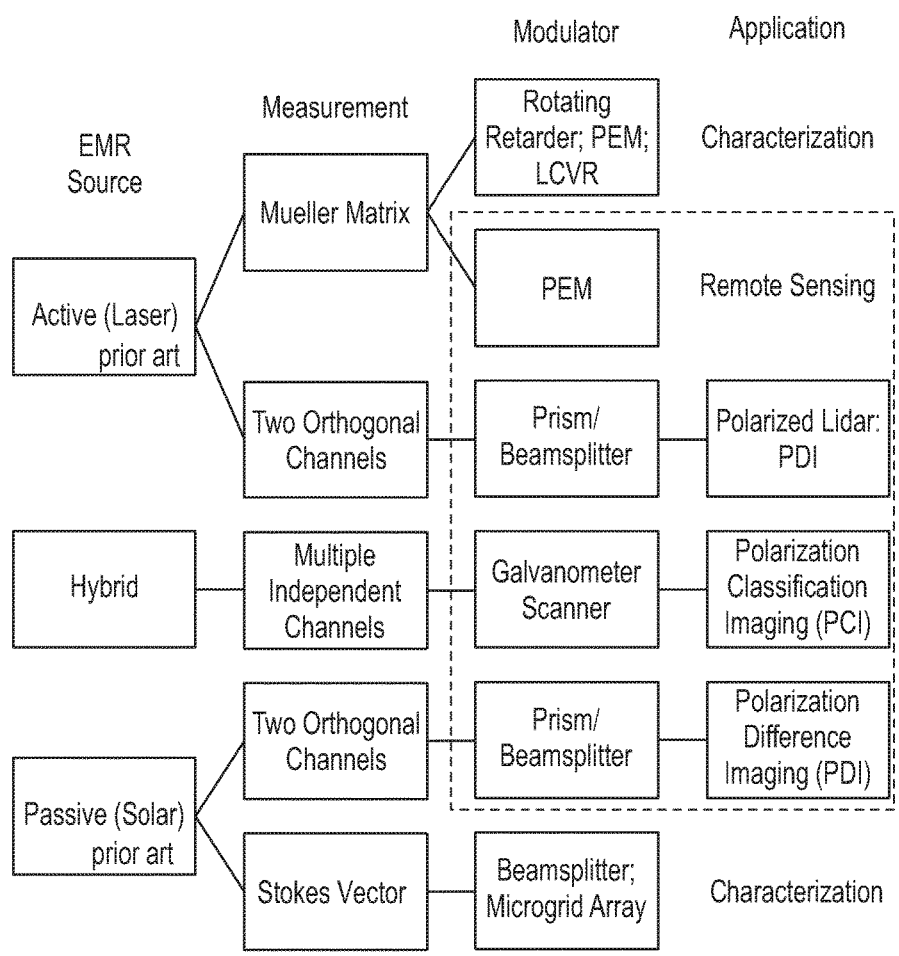
FIG. 1 is a taxonomy of polarimeter types based on electromagnetic-radiation (EMR) source, measurements made, polarization modulators employed, and applications.

The invention can be described in detail, with reference to the figures, by first describing the subspace-projection algorithm used to derive polarimeter channels and corresponding classifiers from the available polarization modulators and a priori Mueller matrices, then describing the specific hardware by which the new polarimeter design can be reduced to practice in a hybrid polarimeter that can achieve data rates up to video-rate in imaging mode with sufficiently small size, weight, and power (SWaP) to allow field implementations.

The subspace-projection algorithm derives what is known in the technical literature as a partial Mueller-matrix polarimeter (pMMP.) The newly disclosed subspace-projection algorithm has advantages over previously published pMMP design methods in that it avoids use of matrix pseudoinverses, which are prone to errors, and imposes no limitations on the objects, materials, or material states that can be observed by the polarimeter. The subspace-projection algorithm is based on application of vector algebra on the vector space of reduced Mueller matrices formed by reducing the measured irradiance as $$I' = I - I_U, \quad (4)$$

where I is the irradiance actually measured by the polarimeter and $I_U$ is the irradiance that a conventional non-polarizing camera would measure with unpolarized illumination. The reduced irradiance I' can be positive or negative. It can be shown that the reduced irradiance is expressible as a vector product of the reduced polarimeter instrument matrix and the reduced Mueller matrix of the illuminated object $$\tilde{M} = [M_{01}\ M_{02}\ M_{03}\ M_{10}\ \ldots\ M_{31}\ M_{32}\ M_{33}]. \quad (5)$$

Construction of reduced Mueller matrices is necessary because conventional Mueller matrices do not form an algebraic vector space. The general pMMP design problem is then stated as follows: Given a target Mueller matrix $M_T$ and a polarimeter configuration defined by a parameter set $\Theta = \{\theta_1, \theta_2, \ldots \theta_Q\}$, determine the set $\Theta$ that maximizes representation of the target matrix in the set of M×N polarimeter irradiance measurements $\{I_{m \times n}\}$, m=1, ..., M and n=1, ..., N. In one embodiment of the invention the parameters $\Theta$ are retarder-waveplate angular orientations, but $\Theta$ can represent any combination of polarization-modulator settings. The algorithm is also general enough to derive channels and classifiers for passive polarimeters. In order to maximize target contrast in a polarimeter measurement, the polarimeter instrument matrix must be chosen to maximize its projection onto the subspace of the reduced target matrix $\tilde{M}'_T$. This subspace-projection can be formalized by defining a differentiable target matrix and applying the gradient operator on the space of reduced Mueller matrices, defined as $$\nabla' \equiv \sum_{i=1}^{15} \hat{M}'_i \frac{\partial}{\partial M'_i}, \quad (6)$$

to the reduced irradiances. The representation of the target in the polarimeter measurement is then maximized by maximizing the contrast parameter, which is a vector dot product, over the set of modulator parameters $\Theta$, that is $$\max_{\Theta} |C| = \max_{\Theta} |\nabla' I' \cdot \nabla' I'_T|. \quad (7)$$

This new polarimeter system and method of use has been validated with field data collected using the main embodiment of the invention. This embodiment can be described in more detail with reference to the figures.

Figure 2:
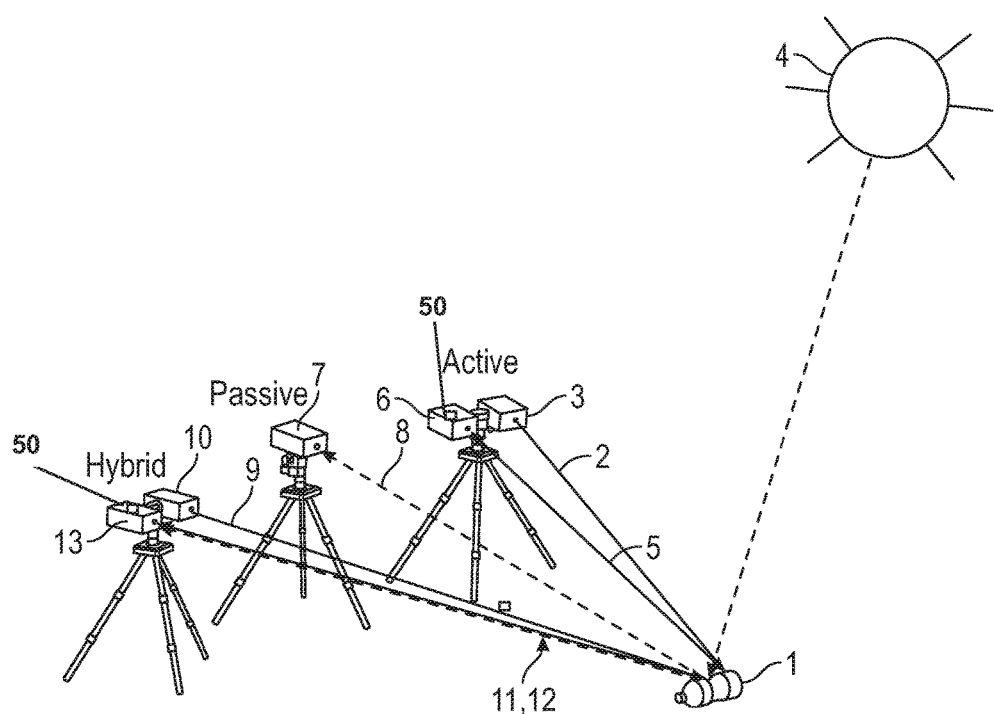
FIG. 2 is an illustration of active monostatic, passive bistatic, and hybrid active-passive sensor geometries.

Field sensors that utilize different electromagnetic-radiation (EMR) sources are illustrated in FIG. 2. The sensor field-of-view (FOV) may be scanned or swept over an area or volume, for instance if the sensor is mounted to a vehicle, or objects may move through a fixed FOV, for instance on a conveyor belt. Each recorded frame may or may not contain a target, although for the purposes of illustration a target is assumed in FIG. 2. The target 1 is illuminated by the probe beam 2, typically a laser beam, that is projected by the sensor transmitter 3. The target may also be illuminated by a passive source 4, which is typically the sun but can also be thermal radiation from the object itself if infrared frequencies are recorded. For active sensors the reflected probe EMR 5 is recorded by the sensor receiver 6, while for passive sensors the receiver 7 records only reflected passive EMR 8. A hybrid active-passive sensor illuminates the target with the probe beam 9 projected by the transmitter 10 and records both the reflected probe EMR 11 and reflected passive EMR 12 in the receiver 13. A polarization modulator 50 is also illustrated.

Figure 3:
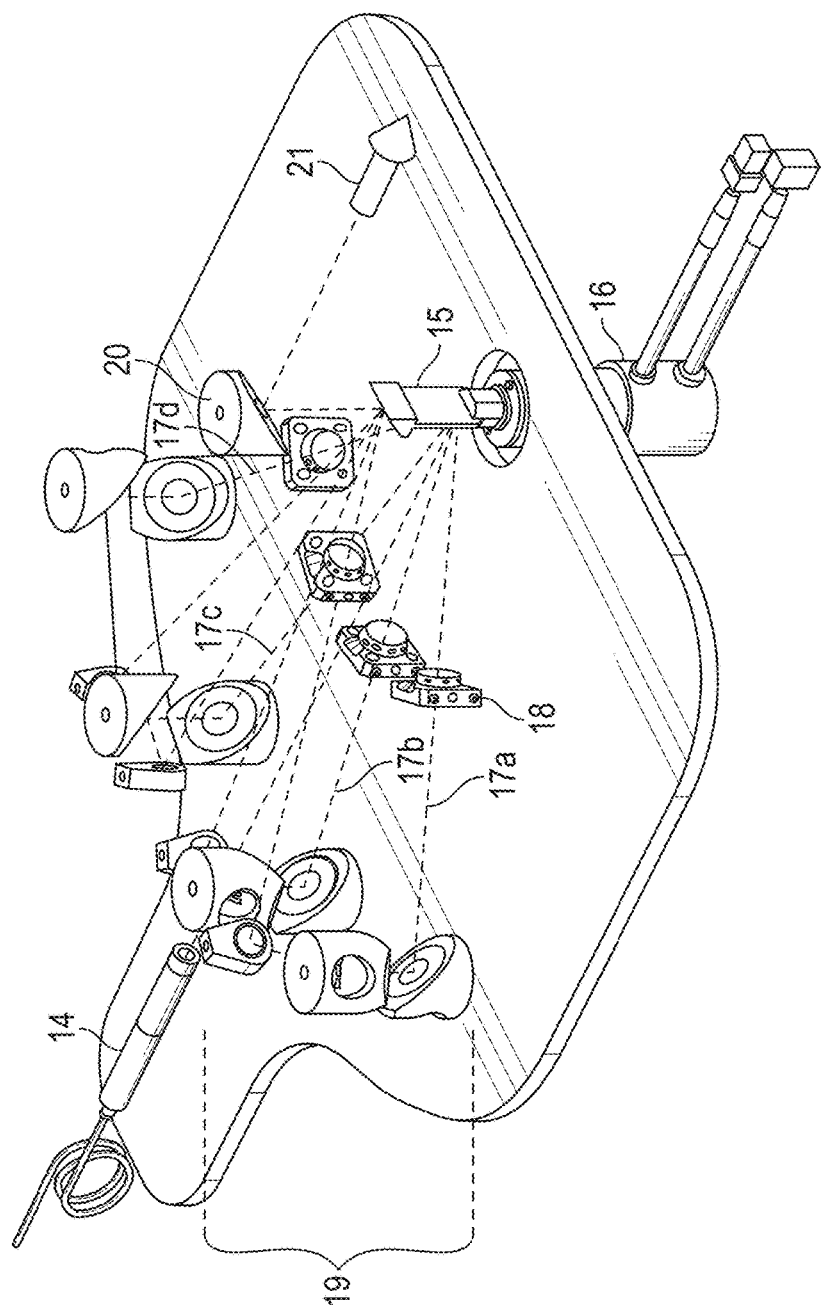
FIG. 3 is an illustration of the polarization multiplexer of an embodiment of the present invention that provides 8 active tunable polarization channels or 4 independent active tunable polarization-difference channels.

New hardware designs as discussed below allow the channels specified by the subspace-projection algorithm to be implemented and corresponding data to be obtained at video rate. The polarization multiplexer is enclosed in the sensor transmitter, embodiments of which are illustrated at 3 and 10 in FIG. 2. The polarization multiplexer is a form of registered-channel multiplexer (RCM). Birefringent crystal waveplates are assumed for the polarization modulators, although other polarization modulators can be used. Conventional polarimeters employ waveplates in rotating hollow-core motors, which can be very accurate but not fast enough to achieve polarization video. As illustrated in FIG. 3, an embodiment of the present invention employs low-inertia scanners, for instance galvanometer scanners, to switch among multiple arms that comprise independent tunable polarization modulators.

Referring to FIG. 3, in one embodiment a laser 14 emits a collimated beam of light that strikes a mirror 15 that is scanned by a galvanometer scanner 16 serially among multiple independent arms 17a-d, each of which, in combination with the static polarizing prism (not shown) in the receiver (not shown), defines a pair of orthogonal channels. During the initial time interval the scanner directs the beam through the first arm 17a, which comprises the first polarization modulator 18, which is set to a channel specified by the subspace-projection algorithm. The modulator 18 may be a rotatable crystal waveplate or a pair of waveplates, but can be other types of polarization modulator as well. Following the polarization modulator the beam is reflected by a fold-mirror assembly 19 back to the scanner mirror 15 and then to the field mirror 20, which reflects the beam toward the field-of-view. The beam is generally expanded or focused by projector lenses located at beam position 21. The scanner dwells on the first arm 17a for a predetermined time interval, then switches to the second arm 17b for a second time interval, generally of the same duration as the first time interval, then switches through the remaining arms 17c-d before rewinding to the first arm 17a and repeating the scan. The subsystem illustrated in FIG. 3 is generally called a polarization-state generator (PSG) and may have more or fewer than 4 arms.

Generally the set of irradiances or images collected for the set of scanner positions, for example 4 positions for the embodiment illustrated in FIG. 3, forms the projection vector used for classification. The dwell time on each arm is determined by the number of arms, the EMR power collected from the FOV, the detector sensitivity, and the sensor speed requirement, and is generally limited by the scanner switching speed. In addition to dwell time the scanner has a characteristic switching time. A typical sum of dwell and switching times with 4 arms and a high-performance galvanometer scanner is 12.5 ms, which implies 50 ms for collection of each image or projection vector. With sufficiently fast data-processing this enables PCI video at 20 frames-per-second. Faster scanners would enable higher data rates.

Figure 4:
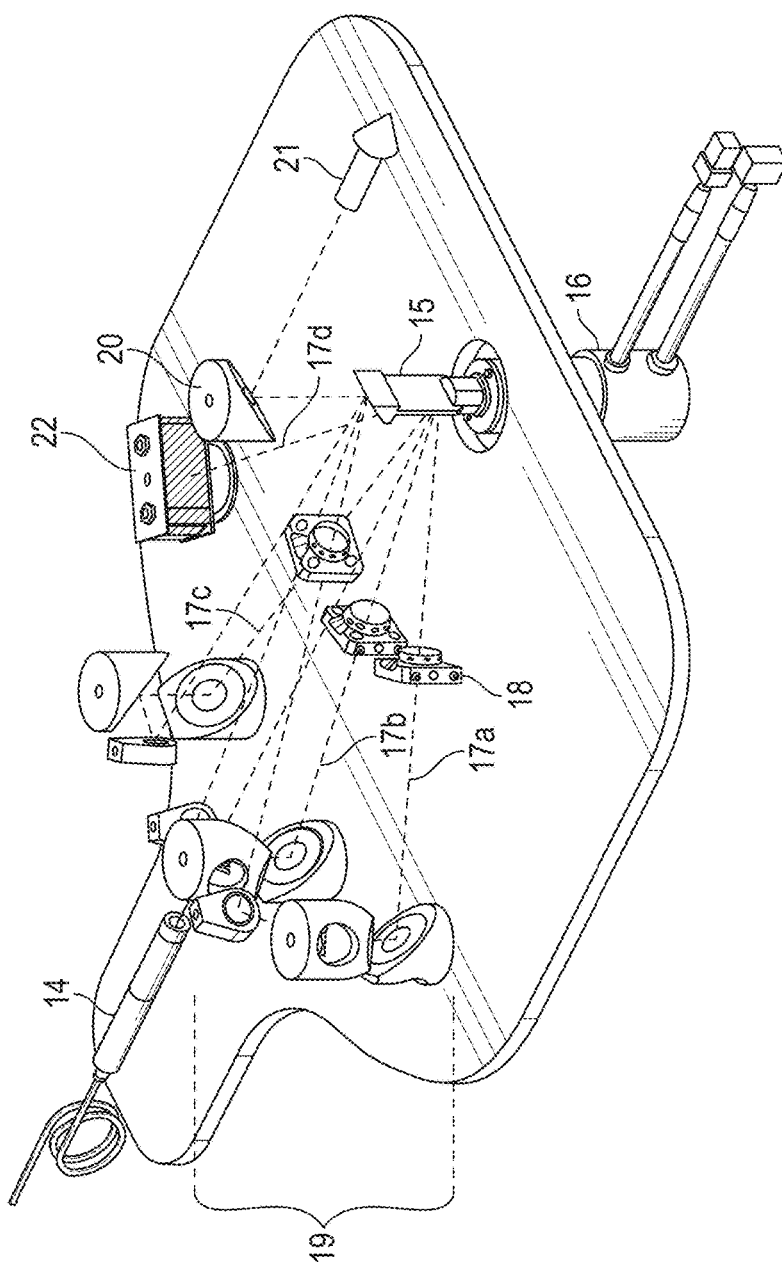
FIG. 4 is an illustration of the polarization multiplexer of an embodiment of the present invention that provides 6 active tunable polarization channels and 2 passive tunable polarization channels.

FIG. 4 illustrates a PSG with a null channel recorded while the scanner dwells on a beam block 22. The null channel records a pair of passive channels that are combined with the active channels obtained from the remaining anus to realize a hybrid active-passive polarimeter. The dwell time on the null channel may be the same, longer, or shorter than the dwell times on the active channels if the reflected power from the passive source is less than or greater than the reflected laser power. The scanner timing signal can provide a reference frequency for lock-in detection.

Figure 5:
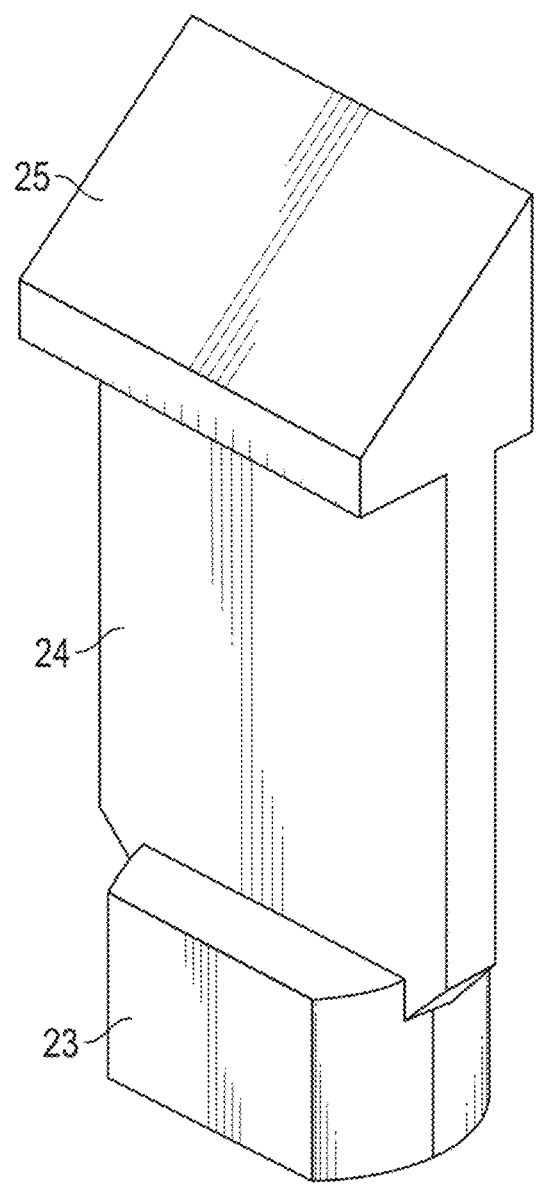
FIG. 5 is an illustration of the composite wedge scanner mirror employed in an embodiment of the present invention.

FIG. 5 illustrates the composite scanner mirror of an embodiment of the present invention. The main parts of the composite scanner mirror are the mounting boss 23, the flat mirror 24, and the wedge mirror 25. The mirrors 24 and 25 must have high optical quality, at least in their central areas, their surfaces must be flush with and centered on the rotation axis, and the entire assembly must have low inertia in order to achieve video-rate data. The composite mirror used for field tests was constructed with 3D-printed plastic parts and has a moment of inertia of 6.4 g/cm$^2$. Alternative embodiments of a galvanometer-based multiplexer can be used, for instance embodiments that do not require the composite wedge mirror. The disclosed polarization multiplexer is a form of registered-channel multiplexer (RCM), which generally switches in time among different channels that produce spatially- and angularly-registered beams at the output. Different forms of RCM can be realized by substituting other modulators for the polarization modulators of the illustrated embodiment of the present invention.

The classification performance and data-processing speed depend on the classification algorithm, a great variety of which may be employed. The classification algorithm, or simply classifier, can be one-dimensional or multi-dimensional, corresponding to the number of measured channels. Two-channel polarimeters typically use one-dimensional classifiers based on the difference between the measured channels, hence the term polarization-difference imaging (PDI.) A one-dimensional classifier makes a positive target classification when the irradiance projection measured in a specified channel is above or below a user-defined threshold, or between two thresholds, and a negative classification otherwise. Classifiers can be defined in terms of the channels derived by the subspace-projection algorithm of the present invention.

Classifiers are described in terms of the bias-variance tradeoff, which balances performance on training datasets with the ability to generalize to unforeseen data. The smallest possible training dataset comprises the target only and results in a high-bias classifier that can perform well on scenes containing the target only but may suffer frequent false-alarms when clutter objects are observed. A one-dimensional classifier based on a channel derived from Eq. 7 of the subspace-projection algorithm is a high-bias classifier. Variance is the ability of the classifier to perform well on scenes that contain target variations and/or background or clutter not represented in the training dataset. Increasing the classifier dimensionality can increase the variance as the target signature can be projected into a higher dimensional space where its projection is more unique. The classifier dimension can be increased by combining two or more channels derived from Eq. 7 of the subspace-projection algorithm. Alternatively or in combination, the classifier bias can be lowered by using a larger training dataset that includes signatures of the background and/or anticipated clutter objects. For example, the background signature can be incorporated by maximizing the generalized contrast parameter R, $$\max_{\Theta} |R| = \max_{\Theta} \left| \frac{\nabla' I' \cdot \nabla' I'_T}{\nabla' I' \cdot \nabla' I'_B} \right|, \quad (8)$$

where the denominator quantifies representation of the background signature in the measured channel, rather than the simple target contrast of Eq. 7. Many other versions of generalized contrast parameter based on channels derived by the subspace-projection algorithm are possible incorporating the background and any number of clutter polarization signatures. It will also be obvious to those skilled in the art of learning algorithms that the subspace-projection algorithm of the current invention can be combined with established algorithms including but not limited to principal-components analysis (PCA) and support-vector machines (SVM) to further generalize the classifier.

In image format the classifier is applied to each pixel independently. Positive classifications can be represented by white pixels with all other pixels black, resulting in binary polarization classification images (PCI) as illustrated in FIG. 6. Binary images are advantageous for fast interpretation and practical data transmission and storage. In the conventional unpolarized image of FIG. 6 the target, the plastic bags 26, are nearly indiscernible from the algae, twigs, and other clutter objects 27, especially if scanning over a large area at video rate, while the PCI reveals the target clearly. The PCI shown in FIG. 6 was obtained in field tests with the main embodiment of the invention in full daylight at 15 m horizontal range.

Figure 7:
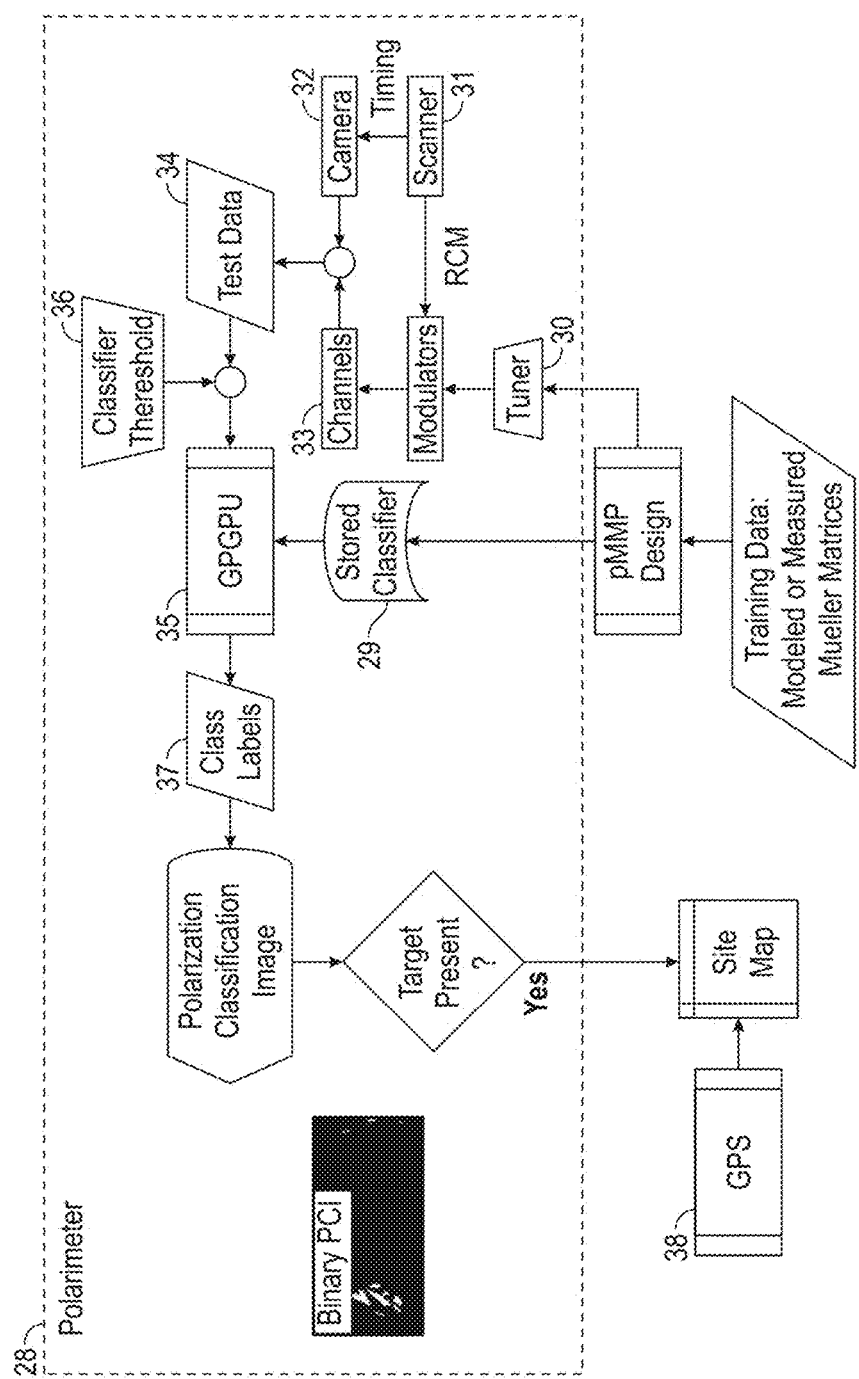
FIG. 7 is a flowchart of an embodiment of the invention designed to map the distribution of a selected material at a test site.
Figure 8B:
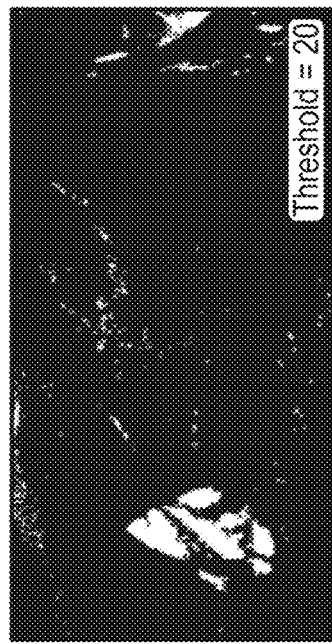
FIG. 8A-D is a set of polarization-classification images (PCI) of plastic bags on a beach obtained using different classifier thresholds.
Figure 8D:
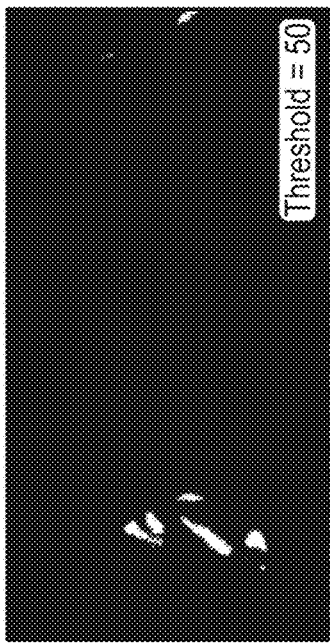
Figure 8A:
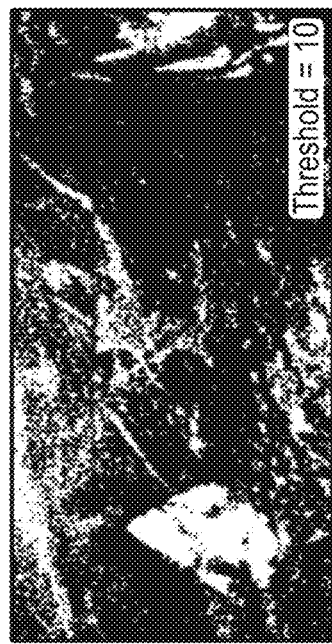
Figure 8C:
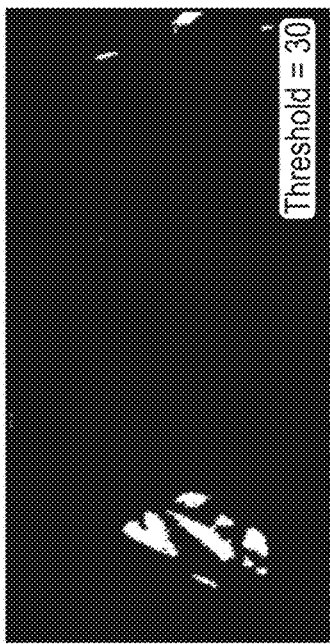

FIG. 7 is a flowchart of an embodiment of the invention designed to map the distribution of a selected material at a test site using a classifier derived by the subspace-projection pMMP-design algorithm. The components inside the dashed box 28 are on-board the field sensor and the flowchart corresponds to a single image or video frame. The sensor field-of-view may be scanned or swept over the test area by a motion system not shown. The subspace-projection pMMP-design algorithm defines the classifier, which is stored in computer memory 29, and the settings of the polarization modulators, which can be changed by the user via the tuner 30. The PSG scanner 31 switches the beam among the independent modulators in the RCM and provides a timing signal to trigger the camera 32 to record corresponding images in the channels 33 defined by the subspace-projection algorithm. These images and the corresponding channel specifications constitute the test data 34 that is input to a real-time processor such as a general-purpose graphics-processing unit (GPGPU) 35. A parallel-processing architecture such as GPGPU is advantageous since each pixel is processed as an independent sensor, although other real-time architectures may be employed. The user can adjust the classifier threshold via the control 36. From these inputs the processor produces the class labels 37, which are 0 or 1 at each pixel for binary PCI. If the target is present in the frame, that is if the frame contains a sufficient number of white pixels, then the frame is stored on the site map with the corresponding global-positioning system (GPS) coordinates provided by an external GPS module 38. With sufficient memory all frames can be stored on the site map. Alternatively each frame can be assigned a class label, 0 or 1, to produce a density map without images. The GPS module and stored site map may also be on-board the sensor.

Figure 6A:
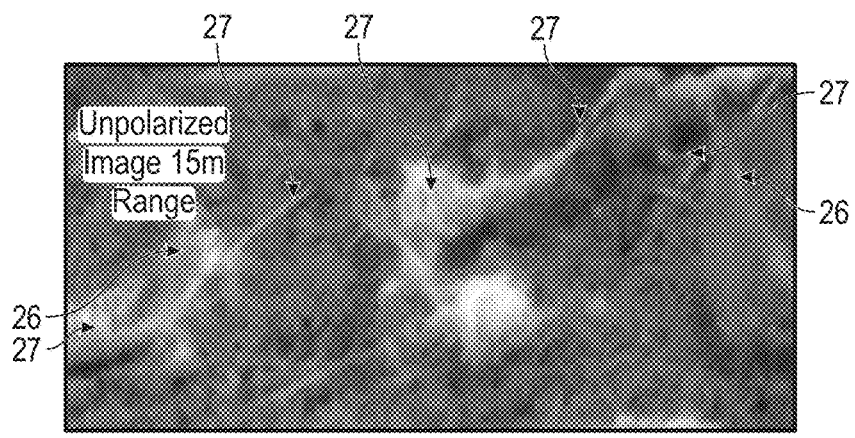
FIG. 6A-B is a comparison of a conventional image and the corresponding polarization-classification image (PCI) of plastic bags on a beach obtained in field tests of an embodiment of the invention at 15 m horizontal range.
Figure 6B:
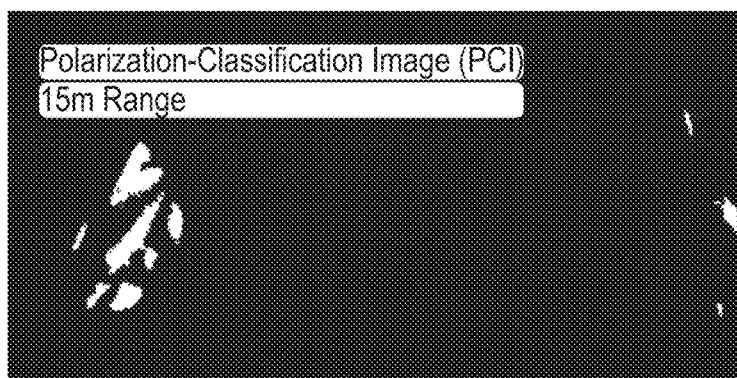

FIG. 8A-D is a set of binary PCIs of the scene illustrated in FIG. 6A obtained by the main embodiment of the invention as the classifier threshold is adjusted.

Both the classifier training and the polarimeter testing and ordinary use are executed by a general or specific-purpose computer or distributed system programmed with computer software implementing the steps described above, which computer software may be in any appropriate computer language, including C++, Python, FORTRAN, BASIC, Java, assembly language, distributed programming languages, etc. The apparatus may also include a plurality of such computers/distributed systems (e.g., connected over the Internet and/or one or more intranets) in a variety of hardware implementations. For example, data processing can be performed by an appropriately programmed microprocessor, computing cloud, field-programmable gate array (FPGA), general-purpose graphics-processing unit (GPGPU), or the like, in conjunction with appropriate memory, network, and bus elements. All computer software disclosed herein may be embodied on any computer-readable medium (including combinations of mediums), including without limitation CD-ROMs, DVD-ROMs, hard drives (local or network storage device), USB keys, other removable drives, ROM, and firmware.

Note that in the specification and the claims the words "a", "an", and "the" mean one or more unless otherwise specified, and the words "about" or "approximately" mean within twenty percent (20%) of the numerical value cited.

Although the invention has been described in detail with particular reference to these embodiments, other embodiments can achieve the same results. Variations and modifications of the present invention will be obvious to those skilled in the art and it is intended to cover all such modifications and equivalents. The entire disclosures of all references, applications, patents, and publications cited above and/or in the attachments, and of the corresponding application(s), are hereby incorporated by reference.

What is claimed is:

1. A registered-channel multiplexer comprising:
   a first scanning element positioned to direct a beam from a controlled source of electromagnetic radiation serially among a set of independent modulators located on a set of independent arms;
   the set of independent modulators, wherein each member of the set of independent modulators defines an independent channel, that is configured to modulate a state of the beam among a set of independent states;
   a second scanning element; and
   the assembly of reflectors located on each independent arm configured to redirect the beam on each independent arm to the second scanning element that redirects the beam from each independent arm to a common path that is pointed at a field-of-view wherein the first scanning element is a scanner mirror attached to a first mechanical scanner that comprises a rotation axis and wherein the assembly of reflectors is an assembly of mirrors and wherein the scanner mirror is a flat mirror parallel to the rotation axis and the second scanning element is a wedge mirror mounted on the first mechanical scanner at an angle to the flat mirror.

2. The registered-channel multiplexer of claim 1 wherein the angle at which the wedge mirror is mounted to the flat mirror is about 45 degrees.

3. The registered-channel multiplexer of claim 1 wherein the set of independent modulators are selected from the group consisting of lenses, polarization modulators, spectral filters, diffractive array generators, holograms, amplitude-phase masks, and any combination thereof.

4. The registered-channel multiplexer of claim 1 wherein one or more members of the set of independent modulators is tunable.

5. The registered-channel multiplexer of claim 1 wherein one or more members of the set of independent modulators is a beam block.

6. A sensor for classifying or recognizing a target within a field-of-view using multiple independent channels comprising:
   a source of controlled electromagnetic radiation positioned in a path with a detector and the field-of-view positioned there between;
   a first scanning element positioned to direct a beam from the source of controlled electromagnetic radiation serially among a first set of independent modulators located on a set of independent arms;
   the first set of independent modulators, wherein each member of the first set of independent modulators defines an independent channel, configured to modulate a state of the beam among a set of independent states;
   a second scanning element;
   an assembly of reflectors located on each independent arm configured to redirect the beam on each independent arm to the second scanning element that redirects the beam from each independent arm to a common path that is pointed at the field-of-view;
   an electromagnetic-radiation receiver positioned to direct electromagnetic radiation reflected from or transmitted by objects within the field-of-view to a second modulator independent of the first set of independent modulators;
   the detector, positioned to receive the electromagnetic radiation from the second modulator, wherein the detector produces a set of signals that are synchronized with the channels formed by the first set of independent modulators and the second modulator; and
   a processor connected with a memory, wherein the processor is configured to execute a classification algorithm stored in the memory by applying a user-adjustable threshold to the set of detector signals to assign a class label to the set of detector signals, wherein the classification algorithm specifies a function of the threshold in terms of the set of channels formed by the first set of independent modulators and the second modulator wherein the first scanning element is a scanner mirror attached to a first mechanical scanner that comprises a rotation axis and wherein the assembly of reflectors is an assembly of mirrors and wherein the scanner mirror is a flat mirror parallel to the rotation axis and the second scanning element is a wedge mirror mounted on the first mechanical scanner at an angle to the flat mirror.

7. The sensor of claim 6 wherein the angle at which the wedge mirror is mounted to the flat mirror is about 45 degrees.

8. The sensor of claim 6 wherein the first set of independent modulators and the second modulator are selected from the group consisting of lenses, polarization modulators, spectral filters, diffractive array generators, holograms, amplitude-phase masks, and any combination thereof.

9. The sensor of claim 6 wherein one or more members of the first set of independent modulators and the second independent modulator are tunable.

10. The sensor of claim 6 wherein one or more members of the first set of independent modulators is a beam block.

11. The sensor of claim 10 wherein the electromagnetic radiation directed by the receiver to the second modulator includes electromagnetic radiation from a passive source illuminating or emanating from objects within the field-of-view.

12. The sensor of claim 11 wherein the electromagnetic radiation directed by the receiver to the second modulator while the scanning element is directed at the beam block produces a detector signal corresponding to a passive channel as a member of the set of detector signals.

13. The sensor of claim 6 wherein the class labels are stored in the memory.

14. The sensor of claim 6 wherein the set of detector signals is a set of registered digital images and a class label is assigned to each pixel to form a digital classification image.

15. The sensor of claim 6 wherein the class label is 0 or 1.

16. The sensor of claim 6 wherein the field-of-view is scanned or swept over an area or a volume by a gimbal or a moving platform on which the sensor is mounted.

17. The sensor of claim 6 wherein the class labels are assigned at a rate of 20 Hz or greater.

18. The sensor of claim 14 wherein the class labels are assigned and the classification image is electronically displayed at a rate of 20 frames-per-second or greater.

19. The sensor of claim 6 wherein the set of detector signals is synchronized with the set of channels formed by the first set of modulators and the second modulator by a lock-in amplifier using a timing signal provided by the first scanning element.

20. A polarimeter for classifying or recognizing a target within a field-of-view using multiple independent polarization channels comprising:
   a source of controlled electromagnetic radiation positioned in a path with a detector and the field-of-view positioned there between;
   a first scanning element positioned to direct a beam from the source of controlled electromagnetic radiation serially among a first set of independent polarization modulators located on a set of independent arms;
   the first set of independent polarization modulators, wherein each member of the first set of independent polarization modulators defines an independent polarization channel, configured to modulate a polarization state of the beam among a set of independent polarization states;
   a second scanning element;
   an assembly of reflectors located on each independent arm configured to redirect the beam on each independent arm to the second scanning element that redirects the beam from each independent arm to a common path that is pointed at the field-of-view;
   an electromagnetic-radiation receiver positioned to direct electromagnetic radiation reflected from or transmitted by objects within the field-of-view to a second polarization modulator independent of the first set of polarization modulators;

the detector, positioned to receive the electromagnetic radiation from the second polarization modulator, wherein the detector produces a set of signals that are synchronized with the channels formed by the first set of polarization modulators and the second polarization modulator; and a processor connected with a memory, wherein the processor is configured to execute a classification algorithm stored in the memory by applying a user-adjustable threshold to the set of detector signals to assign a class label to the set of detector signals, wherein the classification algorithm specifies a function of the threshold in terms of the set of channels formed by the first set of polarization modulators and the second polarization modulator.

21. The polarimeter of claim 20 wherein the first scanning element is a scanner mirror attached to a first mechanical scanner that comprises a rotation axis and wherein the assembly of reflectors is an assembly of mirrors.

22. The polarimeter of claim 21 wherein the scanner mirror is a flat mirror parallel to the rotation axis and the second scanning element is a wedge mirror mounted at an angle to the flat mirror.

23. The polarimeter of claim 22 wherein the angle at which the wedge mirror is mounted to the flat mirror is about 45 degrees.

24. The polarimeter of claim 20 wherein one or more members of the first set of independent polarization modulators and the second independent polarization modulator are tunable.

25. The polarimeter of claim 20 wherein one or more members of the first set of independent polarization modulators is a beam block.

26. The polarimeter of claim 25 wherein the electromagnetic radiation directed by the receiver to the second polarization modulator includes electromagnetic radiation from a passive source illuminating or emanating from objects within the field-of-view.

27. The polarimeter of claim 26 wherein the electromagnetic radiation directed by the receiver to the second polarization modulator while the scanning element is directed at the beam block produces a detector signal corresponding to a passive channel as a member of the set of signals.

28. The polarimeter of claim 20 wherein the channels are defined by a subspace-projection algorithm that applies a gradient operator on a vector space of reduced Mueller matrices and maximizes a resulting contrast parameter.

29. The polarimeter of claim 28 wherein the user-adjustable threshold is a function of the channels derived by the subspace-projection algorithm.

30. The polarimeter of claim 20 wherein the class labels are stored in the memory.

31. The polarimeter of claim 20 wherein the set of detector signals is a set of registered digital images and a class label is assigned to each pixel to form a digital polarization classification image.

32. The polarimeter of claim 20 wherein the class label is 0 or 1.

33. The polarimeter of claim 20 wherein the field-of-view is scanned or swept over an area or a volume by a gimbal or a moving platform on which the polarimeter is mounted.

34. The polarimeter of claim 20 wherein the class labels are assigned at a rate of 20 Hz or greater.

35. The polarimeter of claim 31 wherein the class labels are assigned and the polarization classification image is electronically displayed at a rate of 20 frames-per-second or greater.

36. The polarimeter of claim 20 wherein the set of detector signals is synchronized with the set of channels formed by the first set of polarization modulators and the second polarization modulator by a lock-in amplifier using a timing signal provided by the scanning element.

37. A method for classifying or recognizing a target within a field-of-view using a polarimeter of claim 20 with multiple independent channels comprising:

positioning the source of controlled electromagnetic radiation in a path with the detector with the field-of-view positioned there between;

serially directing with the first scanning element a beam from the controlled source of electromagnetic radiation among the first set of independent polarization modulators located on a set of independent arms;

producing a beam with the first scanning element and the first set of independent polarization modulators, wherein each member of the first set of independent polarization modulators defines an independent polarization channel, configured to modulate a polarization state of the beam among a set of independent polarization states;

redirecting the beam with the assembly of reflectors located on each independent arm to a second scanning element that redirects the beam from each independent arm to a common path that is pointed at the field-of-view;

collecting a portion of the electromagnetic radiation reflected from or transmitted by objects within the field-of-view with an electromagnetic-radiation collector that directs the portion of electromagnetic radiation to a second polarization modulator independent of the first set of polarization modulators; receiving at the detector the electromagnetic radiation from the second polarization modulator wherein the detector produces a set of detector signals that are synchronized with the set of channels formed by the first set of polarization modulators and the second polarization modulator; and applying a classification algorithm and a user-adjustable threshold to the set of detector signals to assign a class label to the set of detector signals, wherein the classification algorithm specifies the function of the threshold in terms of the set of channels formed by the first set of polarization modulators and the second polarization modulator.

38. The method of claim 37 wherein the first scanning element is a scanner mirror attached to a first mechanical scanner that comprises a rotation axis and wherein the assembly of reflectors is an assembly of mirrors.

39. The method of claim 38 wherein the scanner mirror is a composite mirror having a flat mirror parallel to the rotation axis of the first mechanical scanner and the second scanning element is a wedge mirror mounted at an angle to the flat mirror.

40. The method of claim 39 wherein the angle at which the wedge mirror is mounted to the flat mirror is about 45 degrees.

41. The method of claim 40 wherein one or more members of the first set of independent polarization modulators and the second independent polarization modulator are tunable.

42. The method of claim 37 wherein one or more of the members of the first set of independent polarization modulators is a beam block.

43. The method of claim 42 wherein the portion of the electromagnetic radiation collected and directed to the second polarization modulator includes electromagnetic radiation from a passive source illuminating or emanating from objects within the field-of-view.

44. The method of claim 43 wherein the portion of the electromagnetic radiation collected and directed to the second polarization modulator while the scanning element is directed at the beam block produces a detector signal corresponding to a passive channel as a member of the set of detector signals.

45. The method of claim 37 wherein the channels are defined by a subspace-projection algorithm that applies a gradient operator on a vector space of reduced Mueller matrices and maximizes a resulting contrast parameter.

46. The method of claim 45 wherein the user-adjustable threshold is a function of the set of channels derived by the subspace-projection algorithm.

47. The method of claim 37 wherein the class label is stored in a memory.

48. The method of claim 37 wherein the set of detector signals is a set of registered digital images and a class label is assigned to each pixel to form a digital polarization classification image.

49. The method of claim 37 wherein the class label is 0 or 1.

50. The method of claim 37 wherein the field-of-view is scanned or swept over an area or a volume by a gimbal or a moving platform on which the polarimeter is mounted.

51. The method of claim 37 wherein the class labels are assigned at a rate of 20 Hz or greater.

52. The method of claim 48 wherein the class labels are assigned and the polarization classification image is electronically displayed at a rate of 20 frames-per-second or greater.

53. The method of claim 37 wherein the set of detector signals is synchronized with the set of channels formed by the first set of polarization modulators and the second polarization modulator by a lock-in amplifier using a timing signal provided by the scanning element.

* * * * *

UNITED STATES PATENT AND TRADEMARK OFFICE
CERTIFICATE OF CORRECTION

PATENT NO. : 10,540,571 B2
APPLICATION NO. : 15/542064
DATED : January 21, 2020
INVENTOR(S) : Hoover et al.

Page 1 of 1

It is certified that error appears in the above-identified patent and that said Letters Patent is hereby corrected as shown below:

In the Specification

Column 12, Line 15 is replaced as shown:
with the active channels obtained from the remaining arms Signed and Sealed this
Eleventh Day of August, 2020

Andrei Iancu
*Director of the United States Patent and Trademark Office*